US006313125B1

(12) United States Patent (10) Patent No.: US 6,313,125 B1
Carling et al. (45) Date of Patent: Nov. 6, 2001

(54) THERAPEUTICALLY ACTIVE 1,2,4-TRIAZOLO[4.,3-B] PYRIDAZINE DERIVATIVES AS LIGANDS FOR GABA RECEPTORS

(75) Inventors: William Robert Carling, Bishops Stortford; Kevin William Moore, Buntingford; Austin John Reeve, Great Dunmow, all of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/462,974

(22) PCT Filed: Jul. 27, 1998

(86) PCT No.: PCT/GB98/02227

§ 371 Date: Jan. 14, 2000

§ 102(e) Date: Jan. 14, 2000

(87) PCT Pub. No.: WO99/06407

PCT Pub. Date: Feb. 11, 1999

(30) Foreign Application Priority Data

Jul. 29, 1997 (GB) .................................................. 9715977

(51) Int. Cl.[7] ..................... A61K 31/5025; C07D 487/04
(52) U.S. Cl. ........................................... 514/248; 544/234
(58) Field of Search .............................. 544/234; 514/248

(56) References Cited

U.S. PATENT DOCUMENTS 6,200,975 * 3/2001 Carling et al. ........................ 514/248

FOREIGN PATENT DOCUMENTS

| 0 085 840 A1 | 8/1983 | (EP) . |
| 0134946 | 3/1985 | (EP) . |
| WO93/04066 | 3/1993 | (WO) . |
| WO94/26742 | 11/1994 | (WO) . |
| WO98/04559 | 2/1998 | (WO) . |
| WO98/04560 | 2/1998 | (WO) . |

OTHER PUBLICATIONS

Marczynski, Medline Abstract for Brain Research Bulletin, 45, pp. 341–379, 1998.*

R. McNamara et al., Psychobiology, 21 :101–108 (1993).

G. Tarzia et al., Il Farmaco, 64 :3–16 (1989).

G. Tarzia et al., J. Med. Chem., 31:1115–1123 (1988).

J. Potokar et al., Pharmacology and Pathophysiology, 1 :305–315 (1994).

D.I.B. Kerr et al., Med. Res. Rev., 12 :593–636 (1992).

P. Krogsgaard–Larsen et al., J. Med. Chem., 37:2489–2505 (1994).

* cited by examiner

*Primary Examiner*—Emily Bernhardt
(74) *Attorney, Agent, or Firm*—Shu Muk Lee; David L. Rose

(57) ABSTRACT

1,2,4-triazolo[4,3-b]pyridazine derivatives are ligands for $GABA_A$ receptors useful in the treatment of disorders of dementing illnesses.

5 Claims, No Drawings

THERAPEUTICALLY ACTIVE 1,2,4-TRIAZOLO[4.,3-B] PYRIDAZINE DERIVATIVES AS LIGANDS FOR GABA RECEPTORS

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors containing the α5 subunit and are therefore useful in the therapy where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

The present invention provides a compound of the formula (I):

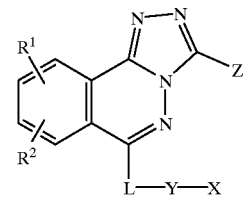

wherein:

$R^1$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

L is O, S or NH;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OCOR^3$, $NR^4R^5$, $NR^4COR^5$, CN or $R^9$, $R^y$ is halogen, $R^3$, $OR^3$, $OCOR^3$, $NR^4R^5$, $NR^4COR^5$ or $CN$ and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl or $CF_3$, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with the nitrogen atom to which they are attached, form a 4–7 membered heteroaliphatic ring containing the nitrogen atom as the sole heteroatom, and $R^9$ is an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylidene optionally substituted by an oxo group or Y is a group $(CH_2)_jO$ wherein the oxygen atom is nearest the group X and j is 2, 3 or 4;

Z is furyl, thienyl or pyridyl each of which is optionally substituted by $R^v$ and/or $R^w$, where $R^v$ is $R^6$, $NR^7R^8$, $NR^7COR^8$, CN, $CF_3$, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$, CN or $CF_3$; and $R^6$, $R^7$ and $R^8$ are respectively independently as defined for $R^3$, $R^4$ and $R^5$;

or a pharmaceutically acceptable salt thereof.

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. Suitable 5-membered rings containing three heteroatoms are 1,2,3-triazoles and 1,2,4-triazoles. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

The term "halogen" as used herein includes fluorine, chlorine, bromine and iodine, of which fluorine and chlorine are preferred.

As used herein the term "$C_{1-4}$alkoxy" includes methoxy and ethoxy groups, and straight-chained, branched and cyclic propoxy and butoxy groups, including cyclopropylmethoxy. Derived expressions such as "$C_{2-4}$alkenyloxy" and "$C_{2-4}$alkyloxy" should be construed in an analogous manner.

$R^1$ is typically hydrogen, fluorine, chlorine, bromine or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or by a pyridyl or phenyl ring each of which rings may be unsubstituted or substituted by one or two halogen atoms or nitro, cyano, amino, methyl or $CF_3$ groups and is generally hydrogen, fluorine or pyridylmethoxy, typically hydrogen.

$R^2$ is typically hydrogen, fluorine, chlorine or bromine, and is generally hydrogen or fluorine, typically hydrogen.

Preferably L is an oxygen atom.

X is generally: pyridyl, pyrazinyl, pyridazinyl or pyrimidinyl optionally substituted by a halogen atom or a group $R^3$, $OR^3$, $NR^4R^5$ or a five membered heteroaromatic ring containing 1, 2 or 3 nitrogen atoms, and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or X is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms. In particular X is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X is optionally fused to a benzene ring, or X is pyrazolyl, isothiazolyl, isoxazolyl, 1,2,4-triazolyl, thiazolyl, 1,2,3-triazolyl or imidazolyl which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$, or X is phenyl which is unsubstituted or substituted by chlorine. Specific values of X are 2-pyridyl, 6-methylpyridin-2-yl, 3-pyridyl, 4-pyridyl, 3,5-dimethylpyrazol-1-yl, 3-methoxypyridin-2-yl, 3-methylisoxazol-5-yl, pyrazol-1-yl, 6-chloropyridin-2-yl, 6-bromopyridin-2-yl, 6-methoxypyridin-2-yl, 6-isopropoxypyridin-2-yl, 6-N,N-dimethylpyridin-2-yl, 6-(imidazol-1-yl)pyridin-2-yl, 3-pyridazino, 4-pyrimidinyl, pyrazin-2-yl, 2-quinolinyl, 2-quinoxalyl, 2-(4-trifluoromethyl)pyridyloxy, 4-methylisothiazolyl, 2,6-dichlorophenyl, 4-methylthiazol-5-yl, 2-methylthiazol-4-yl, 2-[1-(3-trifluoromethyl)pyrid-6-yl]imidazolyl, 1-benzylimidazol-2-yl, 1-(4-chlorophenyl)-1,2,3-triazol-4-yl, 3-chloro-2-methyl-5-trifluoromethylpyrazol-4-yl, 1-methyl-1,2,4-triazol-3-yl, 2-methyl-1,2,4-triazol-3-yl, 4-methyl-1,2,4-triazol-3-yl, 1,2,4-triazol-3-yl, 1-methylimidazol-4-yl and 1-methylimidazol-5-yl.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent.

When X is a substituted 5-membered heteroaromatic ring: $R_x$ is preferably halogen, $R^3$ or a pyridyl, phenyl or benzyl ring which ring is optionally independently substituted by one, two or three halogen atoms or $C_{1-6}$alkyl or $CF_3$ groups and more preferably $R_x$ is methyl, $CF_3$, chlorine or a phenyl, pyridyl or benzyl ring which ring is unsubstituted or substituted by chlorine or $CF_3$; and $R^y$ and $R_z$ are preferably halogen or $R^3$, and more preferably methyl, $CF_3$ or chlorine.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$.

$R^v$ is suitably $R^6$, thienyl, furyl, pyridyl or $NR^7R^8$, for example $C_{1-6}$alkyl, $C_{3-6}$cycloalkyl, hydroxy$C_{1-6}$alkyl, pyridyl, thienyl, or amino and more particularly methyl, ethyl, isopropyl, cyclopropyl, thienyl or pyridyl.

$R^w$ is suitably $R^6$, for example $C_{1-6}$alkyl or hydroxy$C_{1-6}$alkyl, more particularly hydrogen, methyl, ethyl, isopropyl or cyclopropyl. Generally $R^w$ is absent.

Z may be unsubstituted.

Z is preferably a furan. Particular values of Z include fur-2-yl and fur-3-yl.

Generally $R^3$ is $C_{1-6}$alkyl, $C_{1-6}$alkoxy or $CF^3$. In particular $R^3$ is methyl, methoxy, isopropoxy or trifluoromethyl.

Generally $R^4$ and $R^5$ are independently hydrogen or $C_{1-6}$alkyl, in particular hydrogen or methyl, for example both can be methyl.

Generally $R^6$ is $C_{1-6}$alkyl or hydroxy$C_{1-6}$alkyl, for example, methyl, ethyl, isopropyl, cyclopropyl or hydroxymethyl, particularly methyl or cyclopropyl.

Generally $R^7$ and $R^8$ are independently hydrogen or $C_{1-6}$alkyl, particularly hydrogen or methyl.

Generally $R^9$ is pyrazolyl, imidazolyl, phenyl, benzyl or pyridyl optionally substituted by halogen, preferably chlorine, or $CF_3$. In particular $R^9$ can be imidazol-1-yl, 3-trifluoromethylpyrid-5-yl, benzyl and 4-chlorophenyl.

Generally $R^{10}$ is $C_{1-6}$alkyl or $CF_3$, in particular methyl or $CF_3$, for example $CF_3$.

A preferred subclass of compounds is that represented by formula I':

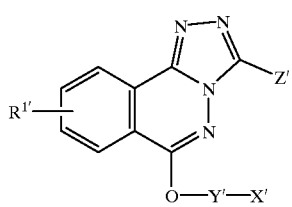

(I')

wherein:
$R^{1'}$ is hydrogen or fluorine;

X' is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X' is optionally fused to a benzene ring, or X' is pyrazolyl, isothiazolyl, isoxazolyl, 1,2,4-triazolyl, thiazolyl, 1,2,3-triazolyl or imidazolyl which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$ or X' is phenyl which is unsubstituted or substituted by chlorine;

Y' is $CH_2$; and
Z' is furan;

or a pharmaceutically acceptable salt thereof.

$R^{1'}$ is preferably hydrogen.

X' is preferably pyridyl optionally substituted by methyl.

For use in medicine, the salts of the compounds of formula I will be pharmaceutically acceptable salts. Hence in a favoured aspect this invention provides the compounds of the formula I and pharmaceutically acceptable salts thereof. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Specific compounds within the scope of the present invention include:
3-(3-furyl)-6-(2-pyridyl)methyloxy-1,2,4triazolo-[3,4-a]phthalazine; and
3-(2-furyl)-6-(2-pyridyl)methyloxy-1,2,4triazolo-[3,4-a]phthalazine; and pharmaceutically acceptable salts thereof.

The compounds of the present invention have a good binding affinity ($K_i$) for the α5 subunit. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the $\alpha 5$ subunit and/or for the enhancement of cognition. Preferably the condition is a dementing illness such as Alzheimer's disease.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the enhancement of cognition, a suitable dosage level is about 0.01 to 250 mg/kg per day, preferably about 0.05 to 100 mg/kg per day, and especially about 0.05 to 5 mg/kg of body weight per day. The compounds may be administered on a regimen of 1 to 4 times per day. In some cases, however, dosage outside these limits may be used.

The compounds in accordance with the present invention may be prepared by a process which comprises reacting a compound of formula III with a compound of formula IV;

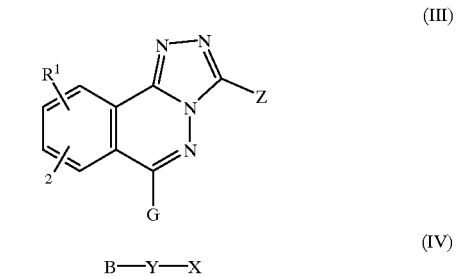

(III)

(IV)

B—Y—X wherein $R^1$, $R^2$, X, Y and Z are as defined above. G is a leaving group such as chlorine and B is LH where L is as defined above. Alternatively, where chemically feasible, G can represent LH where L is as defined above and B is then a leaving group such as chlorine.

Compounds of formula III represent a further feature of the present invention. The groups Z which are preferred for compounds of formula I are preferred for these compounds likewise.

The reaction between compounds III and IV is conveniently effected by stirring the reactants in a suitable solvent, typically N,N-dimethylformamide, in the presence of a strong base such as sodium hydride or lithium bis(trimethylsilyl)amide, typically without heating and under an inert atmosphere such as nitrogen.

The intermediates of formula III above may be prepared by reacting a compound of formula V, which constitutes a further feature of the present invention, with a compound of formula VI:

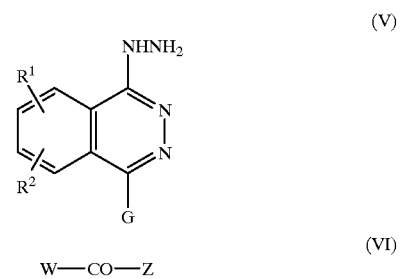

(V)

(VI)

W—CO—Z wherein $R^1$, $R^2$, G and Z are as defined above, and W represents a suitable leaving group such as alkoxy, chlorine or hydroxy.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from room temperature to the reflux temperature of the reaction mixture, for a period of time that depends on the reactants employed and the temperature at which the reaction is carried out. The compound of formula VI may be activated before reaction by reacting with a compound such as bis(2-oxo-3-oxazolidinyl)phosphinic chloride or 1,1'-dicarbonyldiimidazole to form the ketohydrazine.

Compounds of formula III in which G is hydroxy can be prepared by reacting a compound of formula III in which G is chlorine with a base such as sodium hydroxide generally in a solvent such as dioxane, preferably with heating to reflux for a period of about four hours.

The compound of formula V is prepared by reaction of a compound of formula VII:

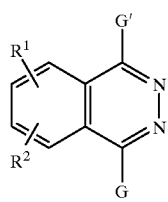

(VII)

where $R^1$, $R^2$ and G are as defined above, and G' is another suitable leaving group which may be the same as or different to G, with hydrazine, usually in the form of its monohydrate, generally in a solvent such as ethanol and generally by refluxing for a suitable period such as 15 minutes to 2 hours.

When the compound of formula VII is asymmetrical, that is $R^1$ and $R^2$ are different or if they are the same, the substitution pattern about the fused benzene ring is not symmetrical, the reaction between this compound and hydrazine will usually give rise to a mixture of isomeric products depending on whether group G or G' is displaced first. Thus in addition to the required product of formula V, the isomeric compound wherein the $R^1$ and $R^2$ moieties are reversed will usually be obtained to some extent. For this reason it will generally be necessary to separate the resulting mixture of isomers by conventional methods such as chromatography.

The compound of formula VII can be used to prepare a compound of formula III in a single step by reacting with the appropriate hydrazoic acid. This is generally carried out in the presence of a base, such as triethylamine, in a solvent such as xylene, at reflux under an inert atmosphere such as nitrogen.

The compound of formula VII can be prepared by reacting a compound of formula X:

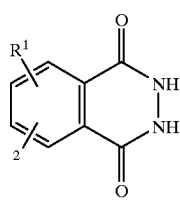

(X)

where $R^1$ and $R^2$ are as defined above, with a suitable reagent for introducing leaving groups G and $G^1$, for example where G and $G^1$ are both chlorine $POCl_3$ can be used generally with heating to reflux for about 16 hours, usually in a solvent.

The compound of formula X can be prepared by reacting a compound of formula XI with hydrazine hydrate ($H_2NNH_2 \cdot H_2O$):

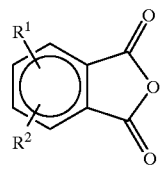

(XI)

where $R^1$ and $R^2$ are as defined above. The reaction is generally carried out in a protic solvent, such as 40% aqueous acetic acid, and in the presence of a buffering agent such as sodium acetate, generally with heating to reflux for about 16 hours.

The compound of formula XI can be prepared by reaction of a compound of formula XII:

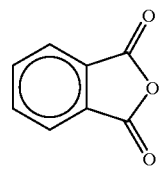

(XII)

with suitable reagents to introduce the substituents $R^1$ and $R^2$ where necessary. For example, when $R^1$ is phenyloxy or pyridyloxy or a derivative thereof, the corresponding hydroxy compound can be used as a reagent. The compound of formula XII is commercially available.

Alternatively, when $R^1$ is the same as G-Y-X in the compound of formula I, it can be introduced by displacing another group $R^1$ which can act as a leaving group, such as fluorine, in the reaction between the compounds of formulae III and IV.

In another procedure, the compounds according to the invention wherein L is O may be prepared by a process which comprises reacting a compound of formula VIII with a compound of formula IX:

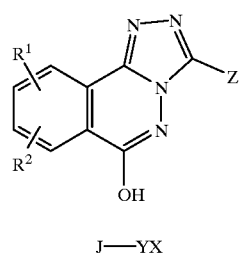

(VIII)

(IX)

wherein $R_1$, $R_2$, X, Y and Z are as defined above and J represents a suitable leaving group such as a halogen atom, typically chlorine. The reaction between compounds VIII and IX is conveniently effected by stirring the reactants in a suitable solvent, typically N,N-dimethylformamide, in the presence of a strong base such as sodium hydride.

The intermediates of formula VIII above may be conveniently prepared by reacting a compound of formula III as defined above with an alkaline hydroxide, e.g. sodium hydroxide. The reaction is conveniently effected in an inert solvent such as 1,4-dioxane, ideally at the reflux temperature of the solvent.

Where they are not commercially available, the starting materials of formula IV, VI, VIII and IX may be prepared by methods analogous to those described in the accompanying Examples, or by standard methods known from the art.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. W. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α5 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration of α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]Ro 15-1788 from the α5 subunit of the human GABA$_A$ receptor of 100 nM or less, preferably 50 nM or less, more preferably 10 nM or less, particularly 5 nM or less and especially 1 nM or less.

EXAMPLE 1

3-(3-Furyl)-6-(2-pyridyl)methyloxy-1,2,4-triazolo[3,4-a]phthalazine a) 1-Chloro-4-hydrazinophthalazine hydrochloride 1,4-Dichlorophthalazine (20.0 g, 0.100 mol) was added to a boiling solution of hydrazine monohydrate (37.3 ml, 0.765 mol) in ethanol (500 ml) and the mixture heated at reflux for 0.5 h. The mixture was cooled to room temperature and the solid collected by filtration. The material was washed with ether, azeotroped with ethanol and dried in vacuo to afford the title-compound. $^1$H NMR (250 MHz, d$^6$-DMSO) δ 7.72–8.35 (4H, m, 4 of Ar—H).

b) 6Chloro-3-(3-furyl)-1,2,4-triazolo[3,4-a]phthalazine 1,1'-Carbonyldiimidazole (0.917 g, 5.65 mmol) was added to a stirred solution of 3-furoic acid (0.634 g, 5.65 mmol) in DMF (30 ml). The solution was stirred for 2 h before adding the preceding hydrazine (1.19 g, 5.14 mmol) and triethylamine (0.71 ml, 5.14 mmol) and triethylamine (0.71 ml, 5.14 mmol). After 18 h at room temperature, the solvent was evaporated in vacuo and water added to the residue. The resultant precipitate was collected by filtration, washed with water and hexane and dried in vacuo to give the ketohydrazine (0.66 g, 45%), MS (ES$^+$) m/e 289 [MH]$^+$. A solution of the ketohydrazine (0.66 g, 2.3 mmol) and triethylamine hydrochloride (0.07 g, 0.5 mmol) in xylene (40 ml) was heated at reflux for 18 h. The solution was cooled to room temperature and the solvent evaporated in vacuo. Diethyl ether was added to the residue and the resulting solid collected by filtration, washed with diethyl ether and dried in vacuo to give the title-phthalazine (0.46 g, 74%), $^1$H NMR (250 MHz, CDCl$_3$) δ 7.32 (1H, d, J=1.8 Hz, Ar—H), 7.62 (1H, d, J=1.4 Hz. Ar—H), 7.90 (1H, m, Ar—H), 8.04 (1H, t, J=7.6 Hz, Ar—H), 8.31 (1H, d, J=8.2 Hz, Ar—H), 8.58 (1H, s, Ar—H), 8.75 (1H, d, Ar—H); MS (ES$^+$) m/e 271 [MH]$^+$.

c) 3-(3-Furyl)-6-(2-pyridyl)methyloxy-1,2,4-triazolo[3,4-a]phthalazine

2-Pyridylcarbinol (0.23 g, 2.1 mmol) was added to a stirred suspension of sodium hydride (0.085 g of a 60% dispersion in oil, 2.1 mmol) in DMF (40 ml) and the mixture stirred at room temperature for 1 h. After this time, the preceding product (0.46 g, 1.69 mmol) was added and the reaction mixture stirred for 18 h. The solvent was removed in vacuo and the residue partitioned between ethyl acetate and water. The organic layer was separated, dried (Na$_2$SO$_4$) and evaporated in vacuo. The residue was chromatographed on silica gel, eluting with 3% ethanol/ethyl acetate and then recrystallised (ethyl acetate) to give the title-compound (0.07 g, 12%). $^1$H NMR (250 MHz, CDCl$_3$), 5.78 (2H, s, CH$_2$), 7.23 (1H, d, J=1.3 Hz, Ar—H), 7.39 (1H, t, J=6.5 Hz, Ar—H), 7.63 (2H, m, 2 of Ar—H), 7.83–7.92 (2H, m, 2 of Ar—H), 8.03 (1H, m, Ar—H), 8.38 (1H, d, J=7.7 Hz, Ar—H), 8.48 (1H, s, Ar—H), 8.60–8.66 (2H, m, 2 of Ar—H); MS (ES$^+$) m/e 344 [MH]$^+$.

EXAMPLE 2

3-(2-Furyl)-6-(2-pyridyl)methyloxy-1,2,4-triazolo[3,4-a]phthalazine a) 6-Chloro-3-(2-furyl)-1,2,4-triazolo[3,4-a]phthalazine Triethylamine (1.46 ml, 10.5 mmol) and 2-furoyl chloride (1.03 ml, 10.4 mmol) were added to a stirred solution of 1-chloro-4-hydrazinophthalazine hydrochloride (2.0 g, 8.7 mmol) in dioxane (200 ml) at room temperature under nitrogen. The mixture was stirred at room temperature for 2 h and then heated at reflux for 6 h. The mixture was cooled to room temperature, the solvent evaporated in vacuo and the residue partitioned between dichloromethane (800 ml) and water (200 ml). The organic layer was separated, washed further with water (4×200 ml) and brine (x 1), dried (MgSO$_4$) and evaporated in vacuo. The residue was chromatographed on silica gel, eluting with a 0.5–2% methanol/dichloromethane gradient, to afford the title-product (0.665 g, 28%); $^1$H NMR (250 MHz, CDCl$_3$) 6.68 (1H, q, J=1.7 Hz, Ar—H), 7.56 (1H, m, Ar—H), 7.73 (1H, m, Ar—H), 7.91 (1H, m, Ar—H), 8.05 (1H, m, Ar—H), 8.31 (1H, d, J=7.5 Hz, Ar—H), 8.76 (1H, m, Ar—H).

b) 3-(2-Furyl)-6-(2-pyridyl)methyloxy-1,2,4-triazolo[3,4-a]phthalazine

The title-compound was prepared from the preceding product using the procedure given for Example 1, part c, mp 205–206° C.; $^1$H NMR (360 MHz, CDCl$_3$) δ 5.78 (2H, s, CH$_2$), 6.63 (1H, m, Ar—H), 7.32 (1H, m, Ar—H), 7.40 (1H, m, Ar—H), 7.62 (1H, d, J=7.9 Hz, Ar—H), 7.67 (1H, m, Ar—H), 7.79–7.83 (2H, m, 2 of Ar—H), 7.93 (1H, m, Ar—H), 8.31 (1H, d, J=7.9 Hz, Ar—H), 8.88–8.92 (2H, m, 2 of Ar—H); MS (ES$^+$) m/e 344 [MH]$^+$; Anal. Found C, 66.22; H, 3.38; N, 20.17. C$_{19}$H$_{13}$N$_5$O$_2$ requires C, 66.46; H, 3.81; N, 20.39%.

What is claimed is:

1. A compound represented by Formula I':

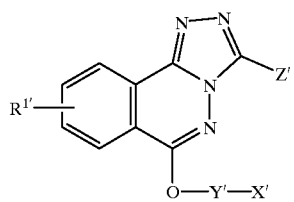

(I')

wherein:

R$^{1'}$ is hydrogen or fluorine;

X' is pyridyl, pyrazinyl, pyridazinyl or pyrimidinyl which is unsubstituted or substituted by methyl, CF$_3$, methoxy, bromine, chlorine, isopropoxy, dimethylamino or X' is substituted by a 5-membered heterocyclic ring having 1, 2 or 3 nitrogen heteroatoms, and X' is optionally fused to a benzene ring, or X' is pyrazolyl, isothiazolyl, isoxazolyl, 1,2,4-triazolyl, thiazolyl, 1,2,3-triazolyl or imidazolyl which is unsubstituted or substituted by one, two or three groups independently chosen from methyl, CF$_3$ and chlorine or is substituted by a phenyl, benzyl or pyridyl ring which ring is unsubstituted or substituted by chlorine or CF$_3$, or X' is phenyl which is unsubstituted or substituted by chlorine;

Y' is CH$_2$; and

Z' is furanyl;

or a pharmaceutically acceptable salt thereof.

2. A pharmaceutical composition comprising an effective amount of one or more compounds according to claim 1 or pharmaceutically acceptable salts thereof and a pharmaceutically acceptable carrier.

3. A method of enhancing spatial learning in a subject suffering from cognition deficit by administering an effective amount of a compound according to claim 1 or a pharmaceutically acceptable salt thereof.

4. A method of enhancing cognition in a subject suffering from Alzheimer's Disease which comprises administering to that subject an effective amount of a compound according to claim 1 or a pharmaceutically acceptable salt thereof.

5. A process for the preparation of a compound according to claim 4 which comprises reacting a compound of formula III with a compound of formula IV:

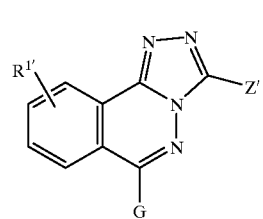

(III)

B—Y'—X'

(IV)

wherein R$^{1'}$, X', Y' and Z' are as defined in claim 4 and either G is a leaving group and B is OH, or B is a leaving group and G is OH.

* * * * *